United States Patent [19]

Olmo et al.

[11] Plant 4,788

[45] Nov. 10, 1981

[54] TABLE GRAPE

[76] Inventors: Harold P. Olmo, Putah Creek Levee Rd.; Albert T. Koyama, 713 Hunt Way, both of, Davis, Calif. 95616

[21] Appl. No.: 115,859

[22] Filed: Jan. 28, 1980

[51] Int. Cl.[3] ..... A01H 5/00

[52] U.S. Cl. ..... Plt./47

[58] Field of Search ..... Plt./47

*Primary Examiner*—James R. Feyrer

*Attorney, Agent, or Firm*—Townsend and Townsend

[57] ABSTRACT

A new and distinct variety of grapevine having early maturing grapes similar to the Perlette variety but which is superior to Perlette by its lack of need for hand thinning of berries and its greater uniformity of and larger berry size than Perlette. The variety is further characterized by its suitability for drying into raisins.

3 Drawing Figures

This invention relates to a new and distinct variety of grapevine of the *vinifera* species to be used as an early maturing seedless table grape variety that is also suitable for drying into raisins.

The new variety is the result of a cross of Gold × Perlette, made at the University of California, Davis, in 1966, and the seedling tested as g4-36 was the most promising in a progeny of 312 vines grown to fruiting in the University vineyard.

Figure 1:
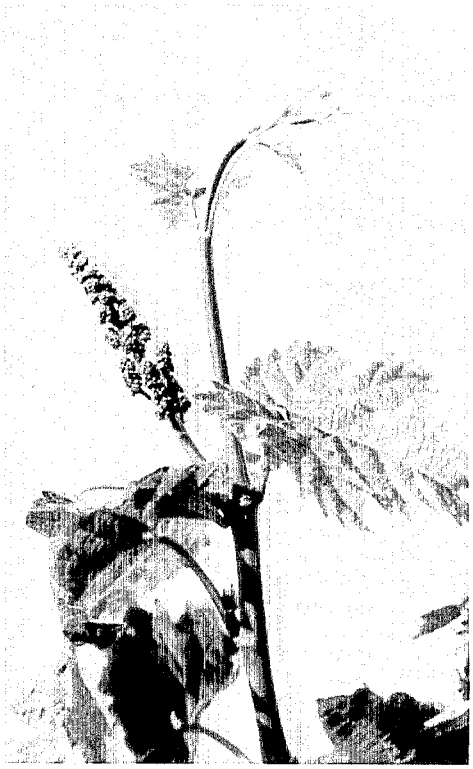
FIG. 1 is a drawing of a typical shoot tip of a plant of the new variety.
Figure 3:
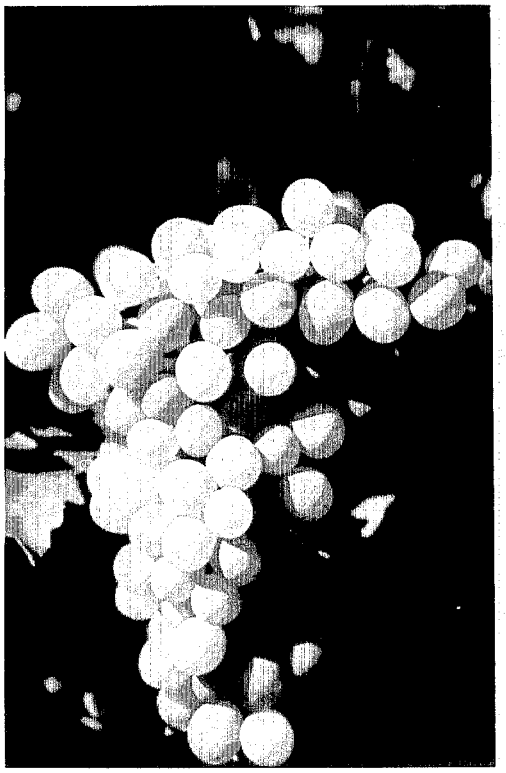
FIG. 3 is a drawing of a typical cluster of the new variety.
Figure 2:
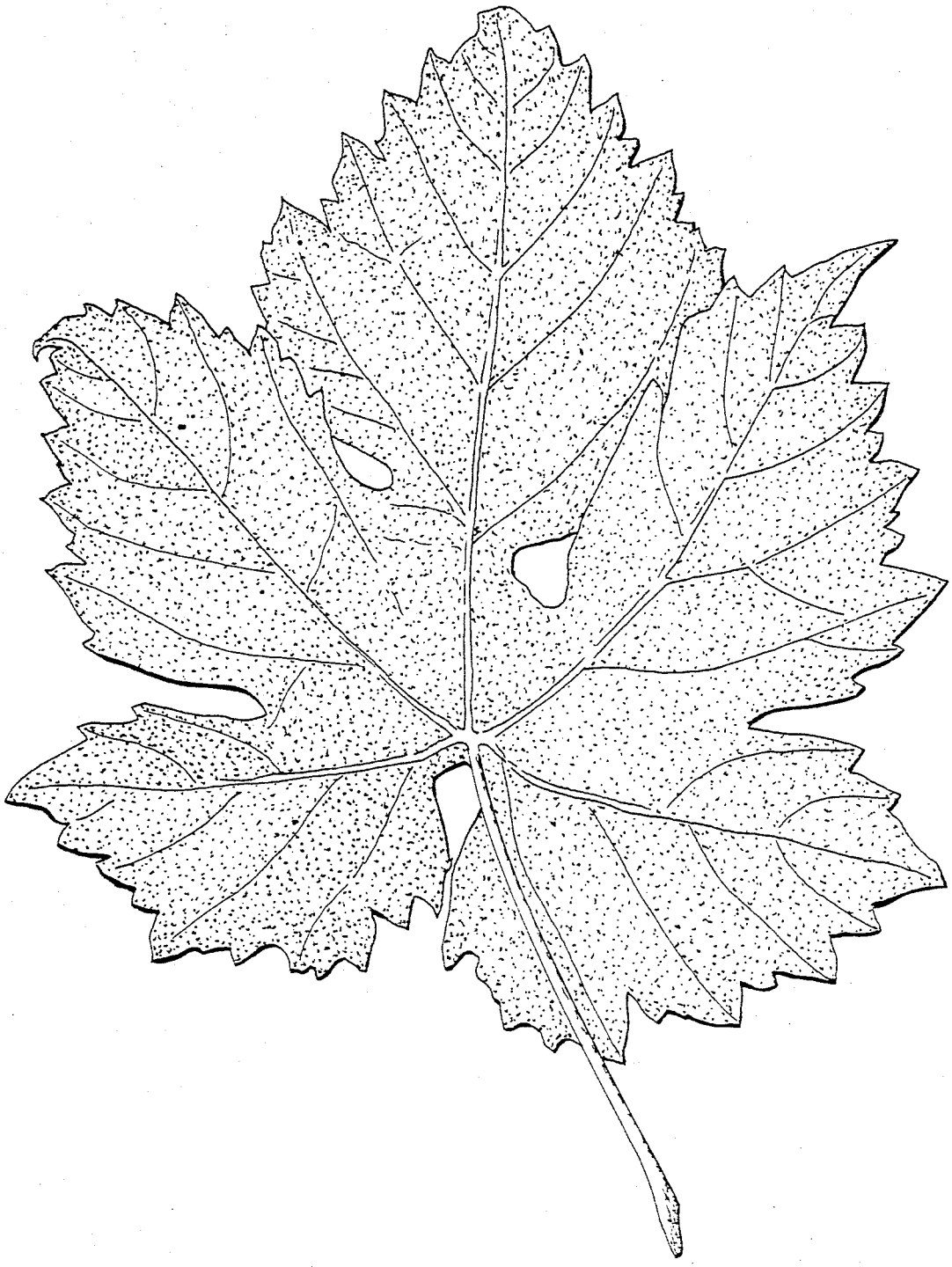
FIG. 2 is a drawing of a leaf typical of the new variety shown reduced from actual size.

The Perlette variety (unpatented) is the earliest seedless grape produced for the commercial market. Although of very good quality and appearance, the cluster sets too compactly and each one must be thinned by hand, a very costly operation. One objective of the present invention was to produce a variety like Perlette, without the necessity of berry thinning. Most early seedless varieties are very low in sugar content, also detracting from their palatability and precluding their use as raisins.

The original vine g4-36 first fruited in 1969 and it was observed to be of interest in 1970 and 1971, because of its general resemblance to Perlette, but had clusters that did not require berry thinning, that were of much greater uniformity and larger berry size.

The original vine was asexually reproduced and increased by yema budding on vines of the rootstock Ganzin 1 on Sept. 9, 1970, at the Kearney Horticultural Field Station. These increases produced vines having the same characteristics as the original. The new variety was also established in cooperative plots with the Coachella Desert Grape Growers League to test its performance in the desert region. These trials began in 1971.

The term yema is a Spanish word meaning eye or bud and refers to a method of grafting grapevines by inserting a bud of the fruiting variety onto the trunk of a rootstock vine already established in its permanent place in the vineyard. The operation is usually done in late summer, the bud is inserted just above ground level, is mounded over with soil and healed in place before winter. In the spring the grafted bud is uncovered, the top of the rootstock is cut off just above the union, and the bud pushes out and is trained up as the fruiting top. Since the bud thus grafted has the advantage of a developed root system beneath it, a large vine can be produced in a short time. The method is also known in California as field budding.

The colors referred to in the following description under the heading Plant Characteristics are subject to substantial variation and are not considered distinctive or diagnostic features of the plant of this invention.

PLANT CHARACTERISTICS

Vine: Vigor medium, less vigorous than Thompson Seedless, trunk of average diameter, relatively few canes, fruitful when spur (two-bud) pruned, budding out several days after Perlette.

Shoot Tip (10"–12"): Very slow to elongate when growth begins, short, very leafy, tip glabrous, reflexed, yellow green, without maroon marking. First flat leaf three-lobed, very thin, glabrous, very shiny, veins depressed, leaf cupped inward, undulated.

Leaf: Bright green, glabrous, large distinctly five-lobed; upper sinuses deep, wide at base, eyelet left from overlapping lobes; basal sinuses deep, narrow, with parallel sides, petiolar sinus wide, open, lyre-shaped with angular borders; apical-teeth on three principal lobes disproportionately long, very acute and curved.

Cluster: Short conical to pyramidal, very uniform, 17.2 cm.×29.2 cm., averaging 955 gm. Length of peduncle to first tendril 1.7 cm., then plus 2.8 cm., to first branch of rachis, fruiting portion 25.2 cm. Average number of berries per cluster 369, wing usually absent; well-filled to slightly compact, shot berries none. Adherence stronger than Thompson Seedless.

Berry: Very uniform in size and shape, short oval, ten largest berries per cluster average 2.2×1.9 cm., 3.5 gms. per berry weight, the range of color of the maturing fruit ready for commercial harvest similar to Perlette, passing from light yellow green, 7.5 GY 9/4 to vivid yellow 2.5 Y 8/12 (Nickerson Color Fan), the bloom is moderate and similar to Perlette, the skin however is much thicker and tougher than Perlette, the berry flesh is firm and meaty but not as crisp as Perlette, the sugar content reaches one to two degrees higher in Balling at an acid range (as tartaric/100 ml juice) of 0.45 to 0.55 gms, like Perlette the fruit is palatable at a low sugar content because of the low acidity, flavor not distinctive, but has a pleasant balance of acid and sugar.

We claim:

1. The new and distinct variety of table grape herein described and illustrated and identified by the characteristics enumerated above.

* * * * *